(12) United States Patent
Kanetake et al.

(10) Patent No.: US 10,974,030 B2
(45) Date of Patent: Apr. 13, 2021

(54) MEDICAL GUIDE WIRE

(71) Applicant: GUNZE LIMITED, Kyoto (JP)

(72) Inventors: Junya Kanetake, Moriyama (JP); Makoto Kawahara, Moriyama (JP); Takashi Kuraoka, Osaka (JP)

(73) Assignee: GUNZE LIMITED, Kyoto (JP)

( * ) Notice: Subject to any disclaimer, the term of this patent is extended or adjusted under 35 U.S.C. 154(b) by 0 days.

(21) Appl. No.: 15/729,756

(22) Filed: Oct. 11, 2017

(65) Prior Publication Data

US 2018/0056042 A1     Mar. 1, 2018

Related U.S. Application Data

(62) Division of application No. 14/649,900, filed as application No. PCT/JP2013/082020 on Nov. 28, 2013, now abandoned.

(30) Foreign Application Priority Data

Dec. 11, 2012  (JP) ................. 2012-270248

(51) Int. Cl.
*A61M 25/09*      (2006.01)
*H05B 6/10*       (2006.01)

(52) U.S. Cl.
CPC ............ *A61M 25/09* (2013.01); *H05B 6/105* (2013.01); *H05B 6/108* (2013.01); *A61M 2025/09083* (2013.01); *A61M 2025/09108* (2013.01)

(58) Field of Classification Search
CPC .................................................... A61M 25/09
See application file for complete search history.

(56) References Cited

U.S. PATENT DOCUMENTS

| | | | | |
|---|---|---|---|---|
| 4,634,042 A | * | 1/1987 | Smith | A61M 25/09 228/173.4 |
| 5,084,022 A | * | 1/1992 | Claude | A61M 25/09 600/585 |
| 6,059,767 A | | 5/2000 | Noriega | |
| 6,511,462 B1 | * | 1/2003 | Itou | A61M 25/0012 264/463 |
| 2002/0151823 A1 | | 10/2002 | Miyata et al. | |
| 2004/0175558 A1 | * | 9/2004 | El-Nounou | A61F 2/958 428/304.4 |

(Continued)

FOREIGN PATENT DOCUMENTS

| | | |
|---|---|---|
| EP | 2 163 276 A1 | 3/2010 |
| JP | H03-073167 A | 3/1991 |

(Continued)

OTHER PUBLICATIONS

JP07328126A English Translation (Year: 1995).*
International Search Report; PCT/JP2013/082020; dated Jan. 21, 2014.

*Primary Examiner* — Daniel L Cerioni
*Assistant Examiner* — Yasmeen S Warsi
(74) *Attorney, Agent, or Firm* — Studebaker & Brackett PC

(57) ABSTRACT

A medical guide wire which can have both slidability and operability and can be easily manufactured is provided. A medical guide wire includes a long flexible wire body, and a wire-like material structure including a wire-like material arranged on the surface of the wire body, in which the wire-like material structure is thermally fused onto the wire body.

12 Claims, 5 Drawing Sheets

(56) References Cited

U.S. PATENT DOCUMENTS

2007/0255217 A1* 11/2007 Burkett ............ A61B 17/12145
  604/164.13
2009/0275862 A1   11/2009 Elsesser
2010/0004561 A1    1/2010 Nabeshima
2012/0197159 A1    8/2012 Miyata et al.

FOREIGN PATENT DOCUMENTS

| JP | 07328126 A | * 12/1995 |
|----|------------|-----------|
| JP | H07-328126 A | 12/1995 |
| JP | 2005-253809 A | 9/2005 |
| JP | 2007-097662 A | 4/2007 |
| JP | 2008-194250 A | 8/2008 |
| JP | 2010-011883 A | 1/2010 |
| JP | 2012-213667 A | 11/2012 |
| WO | 2009/004876 A1 | 1/2009 |

* cited by examiner

MEDICAL GUIDE WIRE

CROSS REFERENCE TO RELATED APPLICATIONS

This application is a Divisional Application of U.S. patent application Ser. No. 14/649,900 filed Jun. 4, 2015, which is the U.S. National Phase Application of International Patent Application No. PCT/JP2013/082020 filed Nov. 28, 2013, which claims benefit of Japanese Patent Application No. 2012-270248 filed Dec. 11, 2012, the entire contents of which are incorporated herein by reference.

TECHNICAL FIELD

The present invention relates to a medical guide wire. For instance, the present invention relates to a medical guide wire used for inserting a catheter into a body cavity, such as a blood vessel or a bile duct.

BACKGROUND ART

Medical guide wires have been used for safely and reliably inserting catheters into cardio-vascular systems or bile ducts. Such a medical guide wire is inserted into a blood vessel or a bile duct, with its distal end projected from the distal end of a catheter, is moved forward in the blood vessel or the like by rotating and pushing or pulling a hand grip portion outside a body, and is inserted into an area near a target portion together with the catheter. In this state, the catheter is moved along the medical guide wire so that its distal end is guided to the area near the target portion. The medical guide wire is thus required to be of high quality to have high flexibility, high slidability in the blood vessel or the like and the catheter, and high operability in the hand grip portion.

A medical guide wire disclosed in Patent Document 1 is known which is for meeting the required quality. The outer periphery of the medical guide wire in Patent Document 1 is divided into three zones differing in lubricity: a high lubricity zone in the outer periphery of a distal end portion including a tip, a low lubricity zone in the outer periphery of a rear end having a certain length including a hand grip portion, and an intermediate lubricity zone in the outer periphery of an intermediate portion between the high lubricity zone and the low lubricity zone. The high lubricity zone includes a lubricating film of a hydrophilic polymer (polyvinylpyrrolidone) having a film thickness of 18 to 20 microns. The intermediate lubricity zone includes a lubricating film of a dilute hydrophilic polymer (polyvinylpyrrolidone) having a film thickness of 5 to 10 microns. The low lubricity zone includes a lubricating film of fluororesin (PTFE).

PRIOR ART DOCUMENT

Patent Document

Patent Document 1: Japanese Unexamined Patent Publication No. 2004-089305

SUMMARY OF THE INVENTION

Problems to be Solved by the Invention

In an attempt to have high slidability, the medical guide wire includes the lubricating film of the hydrophilic polymer formed on the outer periphery of the distal end portion including the tip. However, the medical guide wire cannot have high slidability because it has high contact resistance due to the large contact area between the lubricating film and the inner face of the catheter. Further, the medical guide wire of such a constitution is not excellent in water holding properties of the lubricating film, and is thus difficult to maintain high slidability. This requires re-filling of physiological saline during an operation, and in some cases, stopping of a treatment due to slidability deterioration.

The medical guide wire in Patent Document 1 is divided into three sections, the sections including the different resin films to vary lubricity, thus requiring considerable time and cost for manufacturing the medical guide wire.

The medical guide wire in Patent Document 1 having lubricity also in the hand grip portion is excellent in that the medical guide wire has slidability on the catheter because during the forward movement of the medical guide wire, part of the hand grip portion enters into the catheter. However, the hand grip portion includes the fluororesin (PTFE) lubricating film having a relatively low friction coefficient on the fingers of the operator, and the operator thus cannot increase the gripping force and is likely to slip the hand grip portion from the fingers. This causes the medical guide wire to lack operability in rotating and pushing or pulling the hand grip portion. That is, the conventional medical guide wire is difficult to have both slidability and operability.

To solve such problems, an object of the present invention is to provide a medical guide wire which can have both slidability and operability and can be easily manufactured.

Means for Solving the Problems

The object of the present invention is achieved by a medical guide wire including a long flexible wire body, and a wire-like material structure including a wire-like material arranged on the surface of the wire body, in which the wire-like material structure is thermally fused onto the wire body.

Such a medical guide wire is simply manufactured by, for instance, arranging and heating the wire-like material structure on the surface of the wire body, thus reducing the manufacturing time and the cost. In addition, at inserting the medical guide wire into a catheter or a blood vessel, the outermost portion (top portion) of the wire-like material is brought into contact with the inner wall of the catheter or the like, thus reducing the contact area between the medical guide wire and the catheter or the like to obtain high slidability. In particular, the wire-like material structure includes the wire-like material made of easily-slidable resin fiber, thus obtaining higher slidability. Further, in the hand grip portion rotated and pushed or pulled by the operator, the unevenness (wire-like material structure) formed on the surface of the medical guide wire exhibits a slip prevention function, and allows the operator to increase the gripping force in the hand grip portion for finely rotating and pushing or pulling the hand grip portion, thus obtaining high operability.

In the medical guide wire, preferably, the wire-like material structure includes a thermally-fused portion on the wire body, the thermally-fused portion including a narrow portion narrower than the maximum width of the wire-like material of the wire-like material structure before thermal fusing. In the hand grip portion of the medical guide wire, the narrow portion allows the operator to easily engage the surfaces of the fingers into the wire-like material structure and to increase the gripping force to the medical guide wire, thus obtaining higher operability.

Preferably, the wire-like material structure includes the wire-like material helically wound on the wire body. Such a constitution can greatly improve efficiency in manufacturing the medical guide wire. In addition, the medical guide wire is easily changed in the winding pitch of the wire-like material among its distal end portion, intermediate portion, and hand grip portion, and can thus be manufactured by adding value to the required quality to obtain high slidability in the distal end portion and slidability and operability in the hand grip portion. For instance, the hand grip portion has a large pitch between adjacent portions of the wire-like material, thus enhancing the slip prevention function to improve operability, whereas the distal end portion has a small pitch between adjacent portions of wire-like material, thus obtaining slidability so as to prevent a blood clot from adhering to the distal end portion.

Preferably, the wire-like material structure has meshes. The wire-like material structure having the meshes improves the contact strength in the thermally-fused portion in the wire-like material structure onto the wire body, and is thus effectively prevented from being separated from the wire body. In addition, the meshes include knots mainly brought into contact with the inner wall of the catheter or the blood vessel, and thus reduce the contact area between the wire-like material structure and the catheter or the blood vessel to obtain higher slidability. Further, the hand grip portion of the medical guide wire allows the operator to engage the surfaces of the hand or fingers into the meshes during an operation and to increase the gripping force to the hand grip portion of the medical guide wire, thus enhancing the operability of the medical guide wire.

Preferably, the wire-like material has a non-circular cross section. The wire-like material of the wire-like material structure has the non-circular cross section to enhance the slip prevention function in the hand grip portion, thus improving the operability of the medical guide wire. In the distal end portion of the medical guide wire, only the outermost portion (top portion) of the wire-like material having a non-circular cross section is brought into contact with the inner wall of the catheter or the blood vessel, thus not lowering slidability on the catheter or the blood vessel.

Preferably, the wire body is made of a conductive material, the wire-like material is formed of a material having lower magnetic properties than the wire body, the wire-like material structure is thermally fused onto the wire body in such a way that the wire body is heated by electromagnetic induction from the outside of the wire-like material structure arranged on the wire body, and heat from the heated wire body melts at least one of the opposed regions of the wire-like material structure and the wire body.

Such electromagnetic induction heating which thermally fuses the wire-like material structure onto the wire body effectively prevents the outer surface of the wire-like material structure arranged on the surface of the wire body from being deformed by thermal melting, thus not lowering the slidability of the medical guide wire on the inner wall of the catheter or the blood vessel.

Effects of the Invention

According to the present invention, the medical guide wire can have both slidability and operability and can be easily manufactured.

EMBODIMENTS OF THE INVENTION

Figure 1:
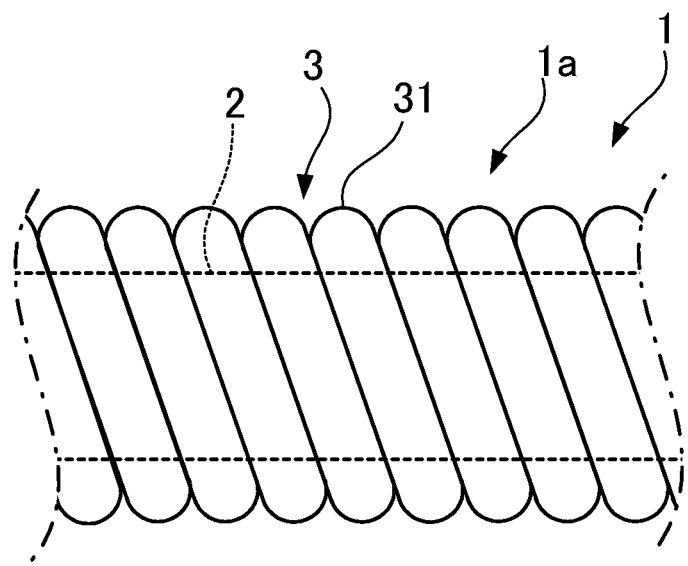
FIG. 1 is a schematic side view of a distal end portion of a medical guide wire according to an embodiment of the present invention.
Figure 2:
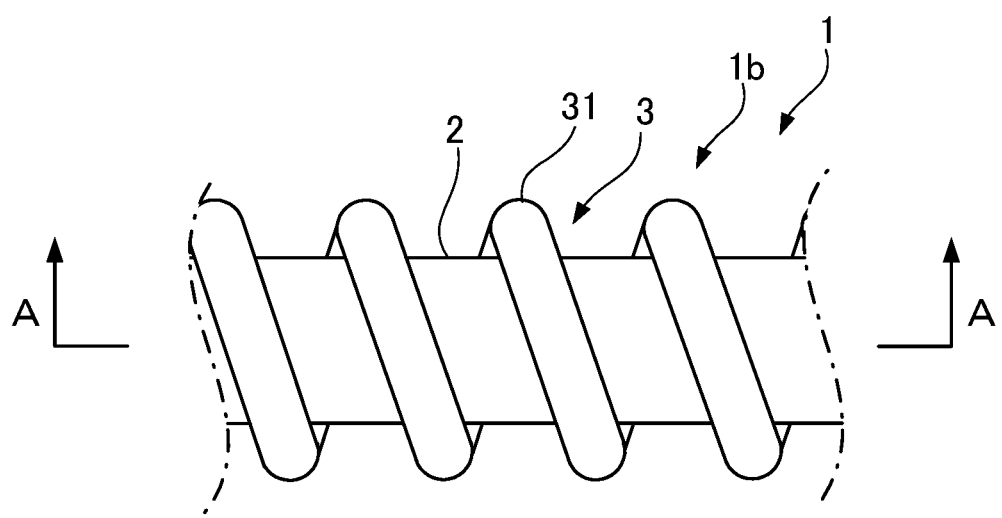
FIG. 2 is a schematic side view of a hand grip portion of the medical guide wire according to the embodiment of the present invention.
Figure 3:
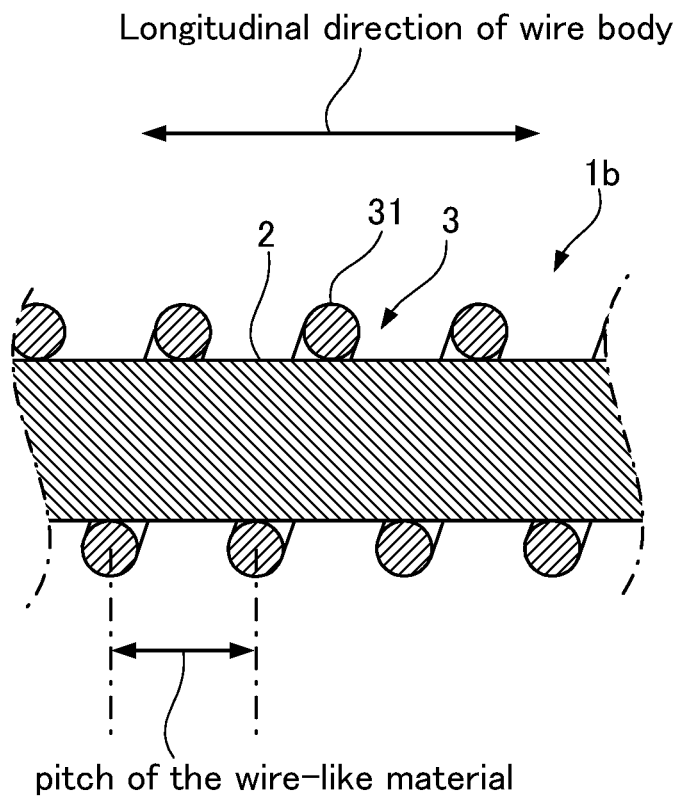
FIG. 3 is a cross-sectional view taken along line A-A in FIG. 2.

Hereinafter, a medical guide wire 1 according to an embodiment of the present invention will be described with reference to the accompanying drawings. The drawings are partially enlarged and reduced in size to facilitate the understanding of the constitution. FIG. 1 is a schematic side view of a distal end portion 1a of the medical guide wire 1 according to the embodiment of the present invention. FIG. 2 is a schematic side view of a hand grip portion 1b of the medical guide wire 1. FIG. 3 is a cross-sectional view taken along line A-A in FIG. 2. For instance, the medical guide wire 1 according to the present invention is inserted into a catheter, and as illustrated in FIGS. 1 to 3, includes a wire body 2, and a wire-like material structure 3 arranged on the surface of the wire body 2.

The wire body 2 is a long flexible wire member. The wire body 2 is made of conventional various materials used as the core material of the medical guide wire. For instance, various metal materials, such as a stainless steel, a piano wire, a cobalt alloy, and an anelastic alloy (including a super-elastic alloy) can be used. In particular, the anelastic alloy (including super-elastic alloy) is preferable, and the super-elastic alloy is more preferable.

The super-elastic alloy is relatively flexible, and has resiliency so that it easily returns to be straight. The wire body 2 of the super-elastic alloy allows the medical guide wire 1 to have high flexibility and resiliency in bending, thus improving followability to a blood vessel or the like which is complicatedly curved and bent, to obtain more excellent operability. In addition, the resiliency of the wire body 2 allows the medical guide wire 1 which is repeatedly curved and bending-deformed to return to be straight, thus preventing lowering of the operability of the medical guide wire 1 due to the bending during use.

The wire body 2 of the cobalt alloy has a high elastic modulus and an appropriate elastic limit. Thus, the wire of the cobalt alloy is excellent in torque transmission, and is hardly buckled. The cobalt alloy should contain a Co element, and is preferably a Co-base alloy having the highest Co content by weight, and more preferably, a Co—Ni—Cr alloy. Such a cobalt alloy makes the above effect more significant. The cobalt alloy having a high elastic modulus and a high elastic limit can be cold-formed, the high elastic limit enabling diameter reduction while sufficiently preventing buckling, thus obtaining flexibility and rigidity sufficient for insertion into a predetermined portion.

The wire body 2 can be in various forms. For instance, the wire body 2 may be formed of one steel material, or may be formed by folding one linear steel material for twisting. The wire body 2 may also be formed by twisting a plurality of linear steel materials, or by twisting a linear steel material and a linear resin member. Further, the wire body 2 can have center and surface portions of different materials, that is, a two-layer structure obtained such that the surface portion is formed by coating thermosetting resin onto the outer surface of the center portion made of a metal. The entire length of the wire body 2 is not limited, but is preferably about 200 to 5000 mm.

The wire body 2 may have an almost constant outside diameter, or a distal end portion whose outside diameter is reduced toward the tip. The wire body 2 including the distal end portion whose outside diameter is reduced toward the tip can be gradually reduced in bending rigidity and twist rigidity toward the tip. This allows the medical guide wire 1 to obtain good passability through narrow portions and flexibility in the distal end portion, thus improving followability to the blood vessel and safety and preventing bending.

The wire body 2 may include a first wire body as the distal end portion, and a second wire body as the intermediate portion and the hand grip portion, the first wire body being connected to the second wire body by welding. In the wire body 2 including the first wire body and the second wire body, the first wire body preferably has a smaller diameter than the second wire body. The portion of the wire body 2 connecting the first wire body to the second wire body is preferably reduced in diameter toward the tip for smooth connection. The wire body 2 of such a constitution can be gradually reduced in bending rigidity and twist rigidity toward the tip. This allows the medical guide wire 1 to obtain good passability through narrow portions and flexibility in the distal end portion, thus improving followability to the blood vessel and safety and preventing bending.

The wire-like material structure 3 arranged on the surface of the wire body 2 includes a wire-like material 31. In the medical guide wire 1 of this embodiment illustrated in FIGS. 1 to 3, the wire-like material 31 is helically wound on the surface of the wire body 2. The wire-like material structure 3 is thermally fused onto and integrated with the wire body 2.

The wire-like material 31 is made of easily-slidable resin fiber, and preferably has the largest diameter of 10 μm or more and 200 μm or less before thermal fusing onto the wire body 2. As the easily-slidable resin fiber, lubricating fluororesin fiber is preferable. Examples of such fluororesin fiber include a tetrafluoroethylene-perfluoroalkyl vinyl ether copolymer (PFA, a melting point of 300° C. to 310° C.), polytetrafluoroethylene (PTFE, a melting point of 330° C.), a tetrafluoroethylene-hexafluoropropylene copolymer (FEP, a melting point of 250° C. to 280° C.), an ethylene-tetrafluoroethylene copolymer (ETFE, a melting point of 260° C. to 270° C.), polyvinylidene fluoride (PVDF, a melting point of 160° C. to 180° C.), polychlorotrifluoroethylene (PCTFE, a melting point of 210° C.), a tetrafluoroethylene-hexafluoropropylene-perfluoroalkyl vinyl ether copolymer (EPE, a melting point of 290° C. to 300° C.), and hydrophobic resin fiber formed of fluororesin, such as copolymers containing these polymers. Among these, PFA, PTFE, FEP, ETFE, and PVDF, which have excellent slidability are preferable. In addition, examples of the easily-slidable resin fiber include hydrophilic resin fiber made of polyvinyl alcohol, polyvinylpyrrolidone, a polyethylene oxide polymer substance, a maleic anhydride polymer substance, an acrylamide polymer substance, and water-soluble nylon. The method for manufacturing the wire-like material 31 by using these resin fibers is not limited. For instance, a conventionally known method in which a raw material is spun by extrusion can be used. Here, the wire-like material 31 made of the easily-slidable resin fiber is manufactured by using the easily-slidable resin alone, or by combining the easily-slidable resins of different types with each other, the easily-slidable resin with a metal material, or the easily-slidable resin with a non-metal material. For instance, the easily-slidable resin fiber is formed by using the hydrophilic resin with thermoplastic resin. As the thermoplastic resin used with the hydrophilic resin, preferably used is a hydrophilic thermoplastic resin that has, in the molecule, a hydrophilic group, such as polyurethane, polyamide, and EVOH, because this enables easy fiber formation by melt spinning, and fiber melting or softening by heating. The method for manufacturing the fiber by using the hydrophilic resin with the thermoplastic resin is not limited, and can include melt kneading and mixing the hydrophilic resin and the thermoplastic resin, forming the hydrophilic resin and the thermoplastic resin into core-sheath, side-by-side, or sea-island conjugate fiber, and using the fibers of the hydrophilic resin and the thermoplastic resin as multi-component fiber such as doubled yarn, piled and twisted yarn, composite spun yarn, and covering yarn. In particular, the hydrophilic resin and the thermoplastic resin are preferably formed into the core-sheath or side-by-side conjugate fiber. The hydrophilic resin and the thermoplastic resin formed into the conjugate fiber can achieve predetermined slidability while maintaining fusion onto the wire body 2 good.

The method for winding the wire-like material 31 on the wire body 2 is not limited. For instance, the wire-like material 31 may be wound on the wire body 2 by using a covering apparatus used for manufacturing covering thread.

The wire-like material 31 may include a single wire, or twisted wires of the same type. The wire-like material 31 may also include twisted wires of different types.

In the wire-like material structure including the wire-like material 31 helically wound on the surface of the wire body 2, adjacent portions of the wire-like material 31 in the direction along the longitudinal direction of the wire body 2 are at predetermined intervals. In this embodiment, in the distal end portion 1a of the medical guide wire, adjacent portions of the wire-like material 31 in the direction along the longitudinal direction of the wire body 2 are brought into contact with each other (there is no interval between the adjacent portions of the wire-like material 31), and in the hand grip portion 1b of the medical guide wire, the pitch of the wire-like material 31 in the direction along the longitudinal direction of the wire body 2 is two to ten times the largest diameter of the wire-like material 31. As illustrated in FIG. 3, the pitch of the wire-like material 31 is the distance between the centers of adjacent portions of the wire-like material 31 in the direction along the longitudinal direction of the wire body 2. To form the medical guide wire, the pitch of the wire-like material 31 can have any value.

The wire-like material structure 3 (the wire-like material 31) is thermally fused onto the outer surface of the wire body 2. To thermally fuse the wire-like material structure 3 (the wire-like material 31) onto the outer surface of the wire body 2, for instance, the wire-like material 31 is helically wound on the outer surface of the wire body 2, and is heated and melted to be thermally fused onto the surface of the wire body 2. For the heating, for instance, a chamber type thermal treatment apparatus is used to provide heat from the outside of the wire-like material 31 wound on the wire body 2. For instance, the thermal fusion includes melting and softening at least a portion of an object by heating to bond the portion onto another object, and also includes softening an object without a melting point or an object made of the hydrophilic resin at a temperature exceeding a glass transition temperature and bonding the object onto another object.

In particular, in a case where the wire body 2 is formed of a conductive material which can easily conduct electricity and the wire-like material 31 is formed of a material having lower magnetic properties than the wire body 2, preferably, the wire-like material 31 is bonded onto the outer surface of the wire body 2 in such a way that the wire body 2 is heated by electromagnetic induction by an electromagnetic induction heating apparatus from the outside of the wire-like material 31 arranged on the wire body 2, and heat from the heated wire body 2 melts at least one of the opposed regions of the wire-like material 31 and the wire body 2 to thermally fuse the wire-like material 31 onto the outer surface of the wire body 2. The material having lower magnetic properties than the wire body 2 also includes a material without magnetic properties. The electromagnetic induction heating is a heating method used for an electromagnetic cooker (IH cooking heater) and high frequency welding; this flows an alternating current to a coil to change a magnetic field (magnetic flux density), and generates an induction current (eddy current) in a conductive substance placed in the magnetic field, the resulting resistance allowing the conductive substance itself to generate heat.

The density of the induction current generated in the wire body 2 heated by electromagnetic induction increases from the center toward the surface of the wire body 2. The wire body 2 is thus concentratively heated in its surface more quickly than its inside. When the wire body 2 has a lower melting point than the wire-like material 31, the concentratively heated surface (the opposed region (contact region) of the wire body 2 opposed to the wire-like material 31) of the wire body 2 is melted. When the wire-like material 31 has a lower melting point than the wire body 2, heat generated from the wire body 2 is transmitted to the wire-like material 31 and melts the opposed region (contact region) of the wire-like material 31 opposed to the wire body 2. The frequency of the electric current flowing through the electromagnetic induction heating apparatus (the alternating current flowing through the coil) is set high, allowing the surface of the wire body 2 to concentratively generate heat. The frequency of the electric current is set low, allowing the inside of the wire body 2 to uniformly generate heat. Thus, the frequency of the electric current flowing through the electromagnetic induction heating apparatus is preferably changeable, as needed.

Such electromagnetic induction heating quickly softens or melts the wire-like material 31 and the wire body 2 on the contact interface thereof and in the vicinity thereof, thus easily maintaining the molecular orientation contributing to the material properties of the wire-like material 31, and maintaining the mechanical strength of the wire-like material 31 high. In addition, unlike heating by heat transmission or radiation from the outside and energy beam irradiation, the wire-like material 31 and the wire body 2 which are softened or melted only on the contact interface thereof and in the vicinity thereof easily maintain the surface unevenness on the outer surface of the medical guide wire 1, thus enhancing slidability.

To bond the wire-like material structure 3 (the wire-like material 31) onto the outer surface of the wire body 2 more strongly, preferably, an adhesive, such as a primer, is coated onto the outer surface of the wire body 2, the wire-like material 31 is wound on the outer surface of the wire body 2 to form the wire-like material structure 3, and the adhesive and the wire-like material structure 3 (the wire-like material 31) are melted by heating to fuse the wire-like material structure 3 (the wire-like material 31) on the wire body 2. The adhesive, such as the primer, preferably contains the same material as that used for the wire-like material. Examples of the material contained in the primer include polyurethane, polyimide, polyamideimide, and precursors thereof. Among these, the primer preferably contains polyimide, polyamide, and precursors thereof, which are not reduced in coating strength at thermal fusing and have high elasticity.

To bond the wire-like material structure 3 (the wire-like material 31) onto the outer surface of the wire body 2 more strongly, the surface of the wire body 2 may be etched before the wire-like material 31 is wound on the wire body 2. The etching forms fine unevenness on the surface of the wire body 2, thus improving the bondability of the wire-like material 31 onto the wire body 2 and enhancing the durability of the medical guide wire 1. The etching method is not particularly limited, and specifically, used are physical etching methods, such as sandblast etching, ion etching, plasma etching, ion milling, and ECR etching, and chemical etching methods, such as wet etching using an etching solution containing nitric acid and hydrofluoric acid or an alkali solution, and dry etching using a mixed gas for generating plasma mainly containing a fluorine-containing gas, such as $CF_4$, and oxygen.

The medical guide wire 1 according to this embodiment of the above constitution is simply manufactured by, for instance, arranging and heating the wire-like material structure 3 on the surface of the wire body 2, thus reducing the manufacturing time and the cost. The conventional medical guide wire is manufactured by coating the resin material onto the wire body to form the film, thus being difficult to maintain the outer shape dimension of the medical guide wire uniform, whereas the medical guide wire 1 of this embodiment is formed by arranging the wire-like material structure 3 including the wire-like material 31 of a predetermined thickness on the surface of the wire body 2 of a predetermined thickness, thus easily maintaining the outer shape dimension of the medical guide wire 1 uniform. Here, before or after thermal fusing of the wire-like material 31, the interval space of the wire-like material 31 (recess portion) and the surface of the wire-like material (projecting portion) can be subjected to coating. The hydrophilic resin coating is preferably provided at the interval space of the wire-like material 31, which enhances the water holding properties of the medical guide wire 1 and prevents sliding deterioration in use to the greatest extent possible. For instance, preferably the wire-like material 31 is formed of a hydrophobic resin and the hydrophilic coating is provided in the recess portion at the interval space of the wire-like material 31, thus effectively exhibiting the water holding properties of the recess portion and high slidability. Examples of the hydrophilic resin which is the material of the hydrophilic coating provided in the recess portion at the interval space of the wire-like material 31 include polyvinyl alcohol, polyvinylpyrrolidone, a polyethylene oxide polymer substance, a maleic anhydride polymer substance, an acrylamide polymer substance, and water-soluble nylon. In addition, for the material of the hydrophilic coating, the hydrophilic resin is preferably used with polyimide, polyamideimide, and precursors thereof, with which the wire-like material can be strongly bonded and durability can be improved.

Figure 4:
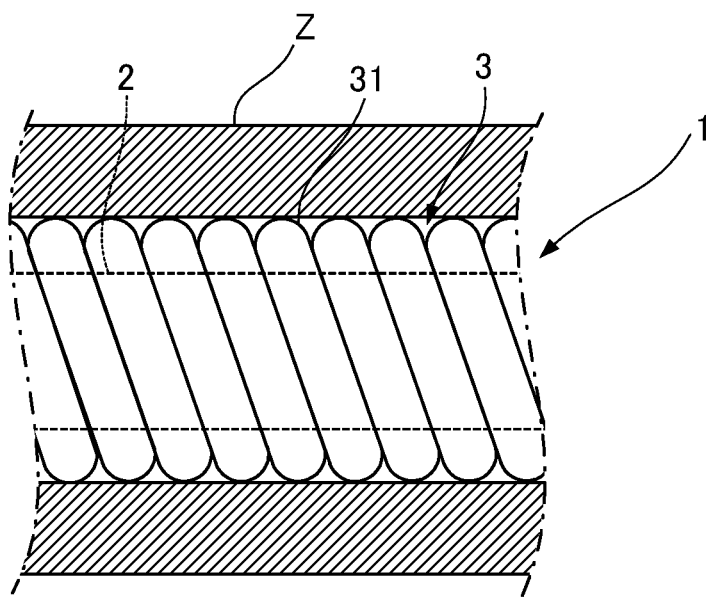
FIG. 4 is an explanatory view illustrating the medical guide wire inserted into a catheter.

As illustrated in FIG. 4, the outermost portion (top portion) of the wire-like material 31 of the wire-like material structure 3 is brought into contact with the inner wall of a catheter Z at inserting the medical guide wire 1 into the catheter or the blood vessel, thus reducing the contact area between the medical guide wire 1 and catheter Z more greatly than the conventional medical guide wire, and lowering the contact resistance between the medical guide wire 1 and catheter Z to obtain high slidability. In particular, the wire-like material structure 3 includes the wire-like material 31 made of the easily-slidable resin fiber, thus obtaining higher slidability. In addition, the wire-like material 31 (the wire-like material structure 3) of the medical guide wire 1 which is formed of the hydrophilic resin fiber to have hydrophilicity is swelled more easily to hold more water, than the lubricating film of the hydrophilic polymer as described in the background art, and exhibits water holding properties in accordance with the shape of the recess shape formed at the interval space of the hydrophilic wire-like material 31, thus ensuring higher slidability. This can effectively prevent sliding deterioration in use. Further, water is effectively held by the wire-like material 31 itself and water is effectively held by the recess portion by virtue of the hydrophilic coating in the recess portion formed at the interval space of the hydrophilic wire-like material 31, and due to the water, the hydrophilic wire-like material 31 effectively exhibits the slidability, thus allowing the medical guide wire 1 to maintain slidability for a long period of time. The medical guide wire 1 of such a constitution avoids the conventional problems of re-filling physiological saline during an operation and of stopping a treatment due to slidability deterioration very effectively.

In the hand grip portion rotated and pushed or pulled by the operator, the unevenness (the wire-like material structure 3) formed on the surface of the medical guide wire exhibits a slip prevention function, and allows the operator to increase the gripping force in the hand grip portion for finely rotating and pushing or pulling the hand grip portion, thus exhibiting high operability. The medical guide wire 1 according to this embodiment can thus have both high slidability and high operability.

In the embodiment, the wire-like material structure 3 includes the wire-like material 31 helically wound on the surface of the wire body 2, thus enabling the medical guide wire 1 to be manufactured very efficiently. In addition, the medical guide wire 1 is easily changed in the winding pitch of the wire-like material 31 among its distal end portion, intermediate portion, and hand grip portion, and can thus be manufactured by adding value to the required quality to obtain high slidability in the distal end portion and slidability and operability in the hand grip portion. For instance, the medical guide wire 1 is manufactured so that the hand grip portion has a relatively large pitch between adjacent portions of the wire-like material 31, thus enhancing the slip prevention function to improve operability, and that the distal end portion has a small pitch between adjacent portions of the wire-like material 31, thus obtaining slidability with a minimum number of step portions to which a blood clot is likely to adhere.

Figure 5:
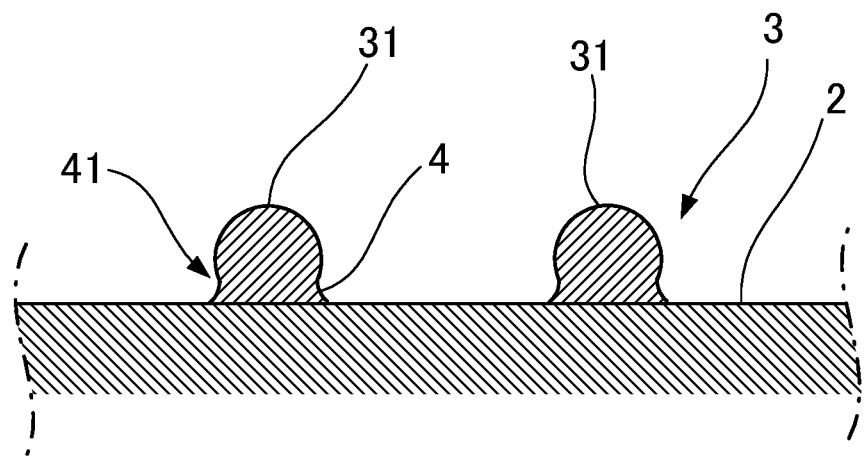
FIG. 5 is an enlarged cross-sectional view of the main components of the medical guide wire illustrated in FIG. 1.

In the medical guide wire 1 of this embodiment, the wire-like material structure 3 is thermally fused onto the surface of the wire body 2. As illustrated in the enlarged cross-sectional view of the main components in FIG. 5, the thermally-fused portion 4 at which the wire-like material structure 3 is thermally-fused onto the wire body 2 may include a narrow portion 41 narrower than the maximum width of the wire-like material 31 of the wire-like material structure 3 before thermal fusing. To form the narrow portion 41 of the thermally-fused portion 4, the portion of the wire-like material 31 of the wire-like material structure 3 brought into contact with the wire body 2 is melted at thermal fusing of the wire-like material structure 3 onto the wire body 2, and is then cooled to be solidified. In this way, the medical guide wire according to this embodiment can include the constricted portion including the narrow portion 41 of the thermally-fused portion 4 in the wire-like material structure 3, thus allowing the operator to easily engage the surfaces of the fingers into the constricted portion (the narrow portion 41) and to increase the gripping force to the medical guide wire 1, and enhancing the operability of the medical guide wire 1. The constricted portion (the narrow portion 41) of the thermally-fused portion 4 is not brought into contact with the inner wall of the catheter, thus not affecting slidability on the catheter. The medical guide wire 1 according to this embodiment is thus excellent to have high slidability and high operability.

The thermal energy amount supplied for thermally fusing the wire-like material structure 3 onto the wire body 2 is changed, as needed, to change the shape of the wire-like material 31 (corresponding to the projecting portion relative to the surface of the wire body 2) of the wire-like material structure 3, thus easily manufacturing the medical guide wire 1 which is suitable for various portions (the artery, vein, and bile duct) of a human body into which the medical guide wire 1 is inserted and for the catheter type, or is specifically excellent in any one of slidability, operability, and blood clot non-adhesion. For instance, in the case where it is desired to actively prevent blood clot adhesion at its distal end portion, the medical guide wire 1 can be formed by supplying much thermal energy to the distal end portion to melt most of the wire-like material 31, and connecting the adjacently arranged portions of the wire-like material 31 to make the surface of the wire-like material structure 3 flat.

Figure 6:
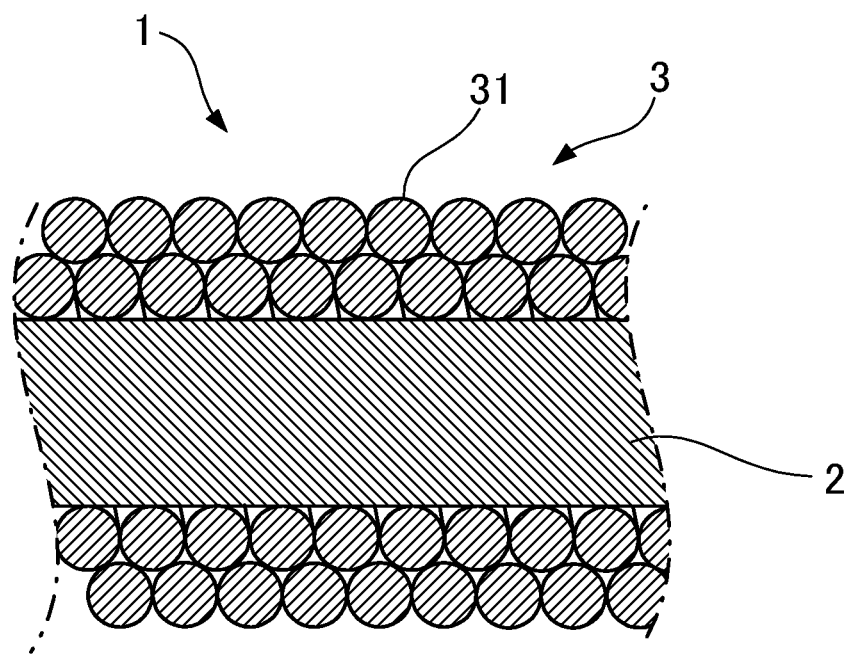
FIG. 6 is a cross-sectional view illustrating a modification of the medical guide wire illustrated in FIG. 1.

Although the medical guide wire 1 according to the present invention has been described above, its specific constitutions are not limited to the embodiment. In the embodiment, as illustrated in FIGS. 1 to 3, the wire-like material structure 3 which covers the outer peripheral surface of the wire body 2 includes one layer of the wire-like material wound on the wire body 2. However, as illustrated in the cross-sectional view in FIG. 6, the wire-like material structure 3 may include a plurality of layers of the wire-like material 31 helically wound on the outer peripheral surface of the wire body 2.

Figure 7:
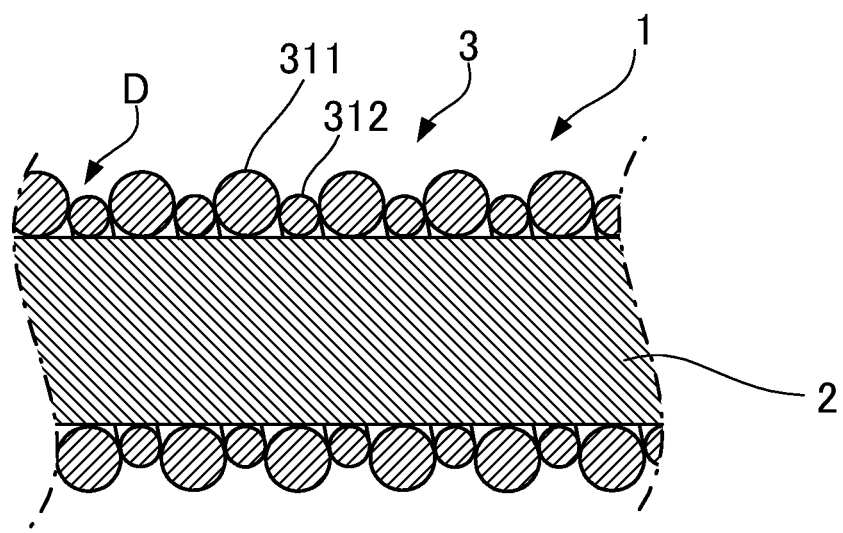
FIG. 7 is a cross-sectional view illustrating another modification of the medical guide wire illustrated in FIG. 1.

In the embodiment, as illustrated in FIGS. 1 to 3, the wire-like material structure includes the single wire-like material 31 helically wound on the outer peripheral surface of the wire body 2. However, for instance, as illustrated in the enlarged cross-sectional view of the main components in FIG. 7, the wire-like material structure 3 may include wire-like materials 311 and 312 of different thicknesses double-helically wound on the outer peripheral surface of the wire body 2. Such a constitution includes a step D formed between adjacent portions of the wire-like materials 311 and 312 of different thicknesses. In the hand grip portion of the medical guide wire 1, the step D exhibits the slip prevention function, thus allowing the operator to increase the gripping force to improve operability. In the distal end portion of the medical guide wire 1, the wire-like material 311 of a large diameter is brought into contact with the inner wall of the catheter, whereas the wire-like material 312 of a small diameter is not brought into contact with the catheter, thus not lowering the slidability of the medical guide wire 1 on the catheter.

Figure 8:
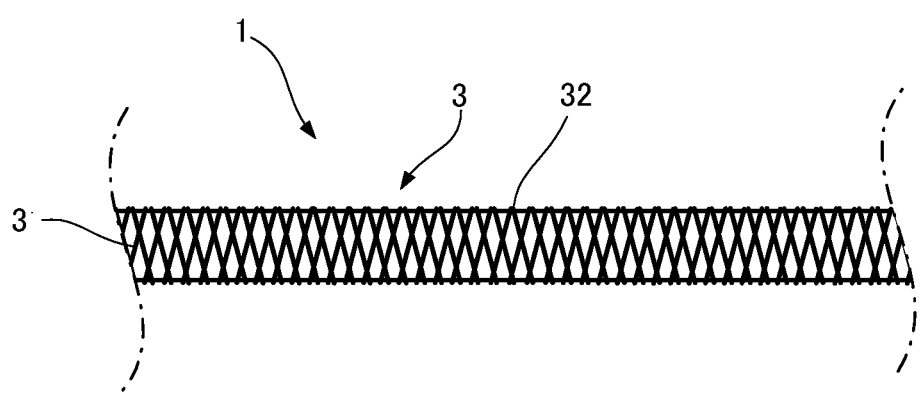
FIG. 8 is a schematic side view illustrating a further modification of the medical guide wire illustrated in FIG. 1.

In the embodiment, the wire-like material structure 3 includes the wire-like material 31 helically wound on the outer surface of the wire body 2. However, for instance, as illustrated in the schematic side view in FIG. 8, the wire-like material structure 3 may include a tubular body 32 with meshes formed of the wire-like material 31 on the outer surface of the wire body 2. The wire-like material structure 3 having the tubular body 32 may be formed in any manner as long as the wire-like material structure 3 has the meshes, and the tubular body 32 may be braided, or be formed by knitting the wire-like material 31. The wire-like material structure 3 which includes the tubular body 32 with the meshes formed of the wire-like material 31 improves the contact strength in the thermally-fused portion in the wire-like material structure 3 onto the wire body 2, and is thus effectively prevented from being separated from the wire body 2. In addition, the meshes include knots mainly brought into contact with the catheter or the blood vessel, and thus reduce the contact area between the wire-like material structure 3 and the catheter or the blood vessel to obtain higher slidability. Further, the hand grip portion of the medical guide wire 1 allows the operator to engage the surfaces of the fingers into the meshes during an operation and to increase the gripping force to the hand grip portion of the medical guide wire 1, thus enhancing the operability of the medical guide wire 1.

Figure 9A:
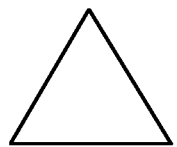
FIGS. 9A to 9I are diagrams for explanation of the shapes of the wire-like material of a wire-like material structure.
Figure 9B:
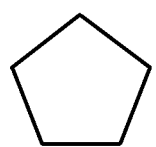
Figure 9C:
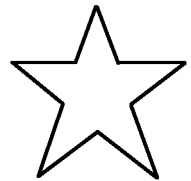
Figure 9D:
Figure 9E:
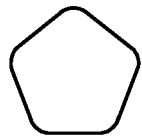
Figure 9F:
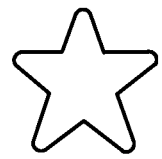
Figure 9G:
Figure 9H:
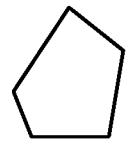
Figure 9I:
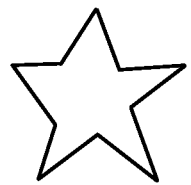

In the embodiment, as illustrated in FIGS. 1 to 3, the medical guide wire 1 includes the wire-like material structure 3 which includes the wire-like material 31 of a circular cross section and covers the outer peripheral surface of the wire body 2. However, instead of the wire-like material 31 of a circular cross section, the wire-like material structure 3 may include the wire-like material 31 of a non-circular cross section including a polygonal cross section, an elliptic cross section, and a fan-shaped cross section. The polygonal cross section of the wire-like material 31 includes polygonal cross sections having sharp corners, and includes, for instance, a triangular cross section illustrated in FIG. 9A, a pentagonal cross section illustrated in FIG. 9B, and a star-shaped cross section illustrated in FIG. 9C. In addition, the polygonal cross section of the wire-like material 31 includes polygonal cross sections having rounded corners, and includes, for instance, a triangular cross section illustrated in FIG. 9D, a pentagonal cross section illustrated in FIG. 9E, and a star-shaped cross section illustrated in FIG. 9F. Further, the polygonal cross section of the wire-like material 31 includes polygonal cross sections of irregularly deformed shapes, and includes, for instance, an irregularly deformed triangular cross section illustrated in FIG. 9G, an irregularly deformed pentagonal cross section illustrated in FIG. 9H, and an irregularly deformed star-shaped cross section illustrated in FIG. 9I. In this way, the wire-like material structure 3 including the wire-like material 31 of a non-circular cross section can have a complicated uneven surface, as compared with the wire-like material structure 3 including the wire-like material 31 of a circular cross section, thus allowing the operator to increase the gripping force in the hand grip portion and improving the operability of the medical guide wire 1. Further, also in the wire-like material structure 3 including the wire-like material 31 of a non-circular cross section, the outermost portion (top portion) of the wire-like material 31 is brought into contact with the inner wall of the catheter or the blood vessel, thus not lowering the slidability of the medical guide wire 1 on the catheter.

Figure 10:
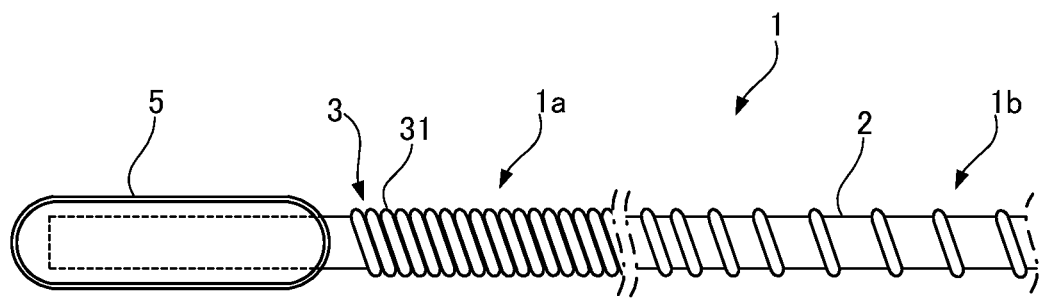
FIG. 10 is a schematic side view illustrating a still another modification of the medical guide wire illustrated in FIG. 1.

In this embodiment, as illustrated in FIG. 10, a covering member 5 may be provided to cover the distal end portion of the wire body 2. The covering member 5 prevents damage to the inner wall of the blood vessel into which the medical guide wire 1 is inserted. The covering member 5 is formed of a thermoplastic elastomer or various rubber materials excellent in flexibility. The covering member 5 is circular tubular so that its distal end and its base end are rounded to prevent damage to the blood vessel. A filler (particles) of a material having imaging contrast properties (radiopaque material) may be distributed into the covering member 5 to form an imaging contrast portion. In addition, the hydrophilic material may be coated onto the outer surface of the covering member 5. This makes the hydrophilic material wet to obtain lubricity, thus reducing the friction (sliding resistance) of the medical guide wire 1 to improve slidability.

DESCRIPTION OF REFERENCE SIGNS 1 medical guide wire
2 wire body
3 wire-like material structure
31 wire-like material
4 thermally-fused portion
41 narrow portion (constricted portion)
5 covering member

The invention claimed is:

1. A method for manufacturing a medical guide wire having an elongated flexible wire body and configured to be inserted into a catheter, the method comprising:
    coating an outer surface of the wire body with a primer;
    after coating the outer surface of the wire body with the primer, arranging a wire material by winding the wire material helically on a surface of the wire body with the primer being disposed between the wire material and the wire body, such that the wire material has a first region facing the wire body and a second region opposing the first region; and
    thermally fusing the wire body and the wire material,
    wherein the wire body is formed of a solid wire member made of a metal material or metal materials,
    the wire material is made of a hydrophobic resin and having a lower melting point than the wire body,
    a material of the primer contains a same material that is used for the wire material, and
    the thermally fusing step includes heating the wire body and melting the first region of the wire material by heat from the heated wire body without melting the second region of the wire material.

2. The method for manufacturing a medical guide wire according to claim 1, wherein the wire material is formed of a material having lower magnetic properties than the wire body.

3. A method for manufacturing a medical guide wire having an elongated flexible wire body and configured to be inserted into a catheter, the method comprising:
    coating an outer surface of the wire body with a primer;
    after coating the outer surface of the wire body with the primer, arranging a wire material by winding the wire material helically on a surface of the wire body with the primer being disposed between the wire material and the wire body, such that the wire material has a first region facing the wire body and a second region opposing the first region; and thermally fusing the wire body and the wire material, wherein the wire body is formed of a solid wire member made of a metal material or metal materials, the wire material is made of a hydrophobic resin and having a lower melting point than the wire body, and a material of the primer contains a same material that is used for the wire material, wherein the thermally fusing step includes thermally fusing the wire body and the wire material by heating the wire body by electromagnetic induction by an electromagnetic induction heating apparatus from an outside of the wire material arranged on the wire body and melting concentratively the first region of the wire material by heat from the heated wire body without melting the second region of the wire material.

4. The method for manufacturing a medical guide wire according to claim 1, further comprising etching an outer surface of the wire body to form unevenness on the outer surface of the wire body to improve bondability of the wire body and the wire material before the step of arranging the wire material by winding the wire material helically.

5. The method for manufacturing a medical guide wire according to claim 1, further comprising coating a recess portion at an interval space of the wire material arranged helically on the wire body with a hydrophilic resin.

6. The method for manufacturing a medical guide wire according to claim 1, wherein in the thermally fusing step, a thermal energy amount supplied for thermally fusing the wire body and the wire material can be changed.

7. The method for manufacturing a medical guide wire according to claim 1, wherein the step of arranging the wire material by winding the wire material helically includes winding a plurality of wire materials of different thicknesses on the surface of the wire body.

8. The method for manufacturing a medical guide wire according to claim 1, wherein the wire material has a non-circular cross section.

9. The method for manufacturing a medical guide wire according to claim 1, wherein the wire body consists of a metal material or metal materials.

10. The method for manufacturing a medical guide wire according to claim 1, wherein the method further comprises cooling the heated wire body and solidifying the melted wire material on the wire body such that adjacent portions of the wire material in a direction along a longitudinal direction of the wire body are at predetermined intervals.

11. The method for manufacturing a medical guide wire according to claim 10, wherein the predetermined intervals between the adjacent portions of the wire material in the direction along the longitudinal direction of the wire body are two to ten times the largest diameter of the wire material.

12. A method for manufacturing a medical guide wire having an elongated flexible wire body and configured to be inserted into a catheter, the method comprising:

coating an outer surface of the wire body with a primer;

after coating the outer surface of the wire body with the primer, arranging a wire material by winding the wire material helically on a surface of the wire body with the primer being disposed between the wire material and the wire body, such that the wire material has a first region facing the wire body and a second region opposing the first region; and thermally fusing the wire body and the wire material, wherein the wire body is formed of a solid wire member made of a metal material or metal materials, the wire material is made of a hydrophobic resin and having a lower melting point than the wire body, a material of the primer contains the hydrophobic resin that is used for the wire material, the hydrophobic resin is a resin selected from a group of fluororesin fibers consisting of a tetrafluoroethylene-perfluoroalkyl vinyl ether copolymer (PFA, a melting point of 300° C. to 310° C.), polytetrafluoroethylene (PTFE, a melting point of 330° C.), a tetrafluoroethylene-hexafluoropropylene copolymer (FEP, a melting point of 250° C. to 280° C.), an ethylene-tetrafluoroethylene copolymer (ETFE, a melting point of 260° C. to 270° C.), polyvinylidene fluoride (PVDF, a melting point of 160° C. to 180° C.), polychlorotrifluoroethylene (PCTFE, a melting point of 210° C.), a tetrafluoroethylene-hexafluoropropylene-perfluoroalkyl vinyl ether copolymer (EPE, a melting point of 290° C. to 300° C.), and copolymers containing any of the fluororesin fibers, and the thermally fusing step includes heating the wire body and melting the first region of the wire material by heat from the heated wire body without melting the second region of the wire material.

* * * * *